United States Patent
Oberlaender et al.

(10) Patent No.: US 9,622,776 B2
(45) Date of Patent: Apr. 18, 2017

(54) SEALING DEVICE FOR SEALING A PASSAGE FOR A MEDICAL INSTRUMENT

(71) Applicant: Karl Storz GmbH & Co. KG, Tuttlingen (DE)

(72) Inventors: Martin Oberlaender, Engen (DE); Sebastian Wagner, Bretten (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 437 days.

(21) Appl. No.: 14/169,890

(22) Filed: Jan. 31, 2014

(65) Prior Publication Data

US 2014/0222022 A1    Aug. 7, 2014

(30) Foreign Application Priority Data

Feb. 1, 2013   (DE) .................. 10 2013 101 019

(51) Int. Cl.
*A61B 17/34* (2006.01)
*A61B 17/00* (2006.01)

(52) U.S. Cl.
CPC .... *A61B 17/3423* (2013.01); *A61B 17/00234* (2013.01); *A61B 17/3462* (2013.01); *A61B 2017/3419* (2013.01); *A61B 2017/3464* (2013.01)

(58) Field of Classification Search
CPC .......... A61B 17/3423; A61B 17/00234; A61B 17/3462; A61B 2017/3419; A61B 2017/3464
See application file for complete search history.

(56) References Cited

U.S. PATENT DOCUMENTS

| | | | |
|---|---|---|---|
| 4,430,081 A | 2/1984 | Timmermans | |
| 4,857,062 A | 8/1989 | Russell | |
| 5,273,545 A * | 12/1993 | Hunt .................. | A61B 17/3498 137/849 |
| 5,350,363 A | 9/1994 | Goode et al. | |
| 5,366,446 A | 11/1994 | Tal et al. | |
| 5,549,594 A * | 8/1996 | Brunken ............ | A61B 1/00137 606/1 |
| 5,628,732 A | 5/1997 | Antoon, Jr. et al. | |
| 5,779,697 A | 7/1998 | Glowa et al. | |
| 5,820,604 A | 10/1998 | Fox et al. | |

(Continued)

FOREIGN PATENT DOCUMENTS

| | | |
|---|---|---|
| DE | 69329286 T2 | 12/2000 |
| DE | 19955071 C1 | 4/2001 |

(Continued)

*Primary Examiner* — Emily Schmidt
*Assistant Examiner* — Lauren M Peng
(74) *Attorney, Agent, or Firm* — Whitmyer IP Group LLC

(57) ABSTRACT

A sealing device for a medical instrument includes a fastening area and a sealing area designed to either bear on the circumference of a medical instrument inserted into the sealing device or to close the sealing device when no medical instrument is inserted. The sealing device further includes a first elastic wall enclosing the sealing area in a ring shape, with an annular first edge, which is connected to the sealing area, and an annular second edge, and a second elastic wall which encloses the first wall in a ring shape and is spaced apart there from, with an annular first edge and an annular second edge, which is connected to the fastening area.

14 Claims, 2 Drawing Sheets

(56) References Cited

U.S. PATENT DOCUMENTS

| | | | | |
|---|---|---|---|---|
| 6,066,117 A | * | 5/2000 | Fox | A61B 17/3462 137/847 |
| 6,217,555 B1 | * | 4/2001 | Hart | A61B 17/3462 128/DIG. 26 |
| 6,419,670 B1 | * | 7/2002 | Dikeman | A61J 15/0015 604/533 |
| 6,551,282 B1 | | 4/2003 | Exline et al. | |
| 7,803,135 B2 | * | 9/2010 | Franer | A61B 17/3462 604/164.01 |
| 2005/0288622 A1 | | 12/2005 | Albrecht et al. | |
| 2008/0171987 A1 | | 7/2008 | Franer et al. | |
| 2009/0240204 A1 | * | 9/2009 | Taylor | A61B 17/3462 604/167.03 |

FOREIGN PATENT DOCUMENTS

| | | |
|---|---|---|
| DE | 102011088336 A1 | 6/2013 |
| EP | 0536549 A1 | 4/1993 |
| EP | 0630660 A1 | 12/1994 |
| EP | 0746359 B1 | 12/1996 |
| EP | 1269925 A1 | 1/2003 |
| EP | 1350476 A1 | 10/2003 |
| WO | 9112838 A1 | 9/1991 |
| WO | 9301850 A1 | 2/1993 |
| WO | 9401149 A1 | 1/1994 |
| WO | 9832484 A1 | 7/1998 |
| WO | 2010045702 A1 | 4/2010 |

\* cited by examiner

Fig. 4
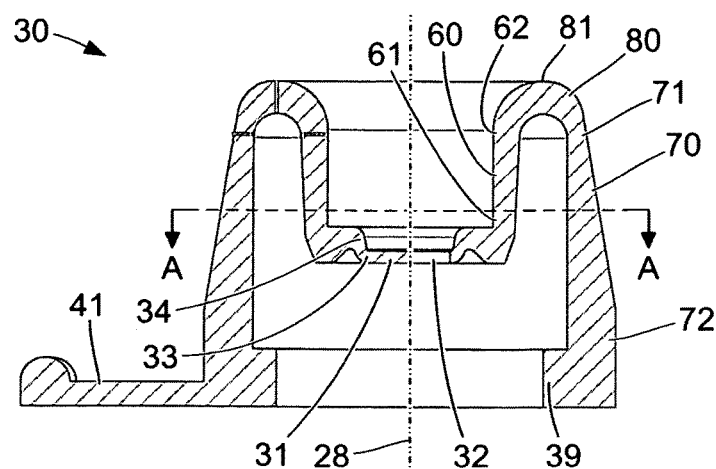
Fig. 5  A-A
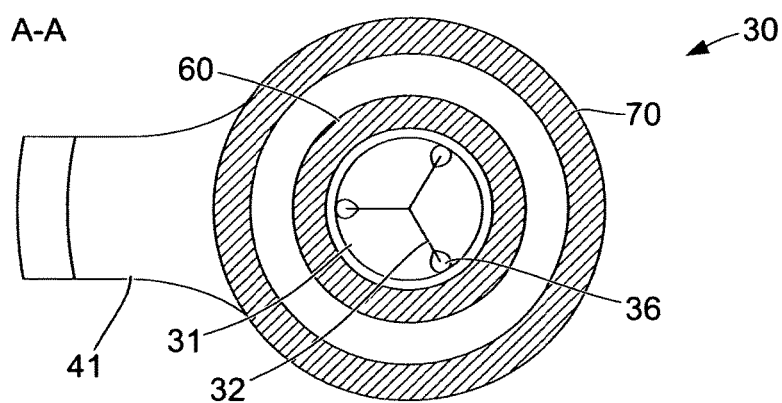
Fig. 6
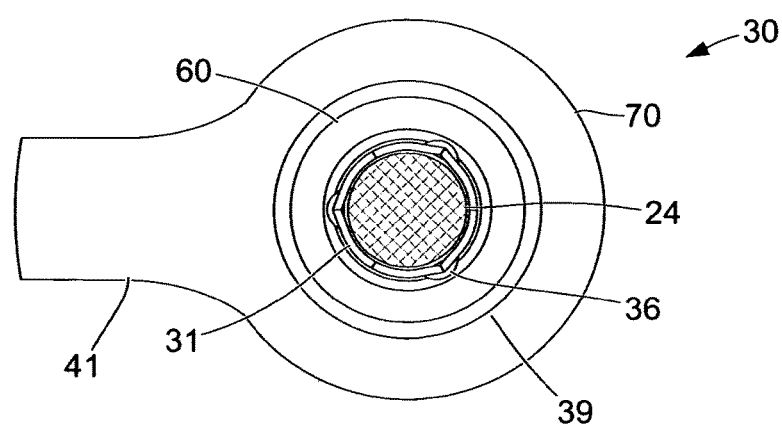

SEALING DEVICE FOR SEALING A PASSAGE FOR A MEDICAL INSTRUMENT

FIELD OF THE INVENTION

The present invention relates to a sealing device for sealing a passage for a medical instrument, in particular for sealing a tube through which an endoscope and/or other medical instruments can be inserted into a natural or artificial body cavity in a microinvasive medical intervention, or for sealing a work channel of an endoscope.

BACKGROUND OF THE INVENTION

Laparoscopy is one example of a microinvasive medical method. By means of a trocar, an artificial access route to the abdominal cavity of a patient is created through the abdominal wall. Through the lumen of a tube of the trocar that remains in the abdominal wall during the laparoscopic intervention, it is possible for an endoscope and/or other medical instruments (for example forceps, scissors, needle holders) to be inserted into the abdominal cavity. During the laparoscopy, the abdominal space is filled carbon dioxide or another gas in order to create a pneumoperitoneum, a hollow space permitting the medical intervention. Without special measures, this gas would escape through the lumen of the tube of the trocar. Therefore, numerous solutions were developed with the aim of closing the lumen of the tube of a trocar in a manner that is as fluid-tight as possible, specifically both in the empty state and also with an instrument inserted. Partially similar problems may arise in a work channel of an endoscope or when inserting a catheter into a blood vessel. In the latter case, however, it is not the escape of gas that is to be prevented, but the escape of blood.

U.S. Pat. No. 4,857,062 describes a valve for inserting a catheter into an artery. For sealing purposes, a duckbill-shaped first element is provided, and a second flexible element which is compressed by a catheter in order to form a fluid-tight seal. Both elements are arranged one behind the other and rigidly in a housing.

WO 93/01850 A1 describes a lever-actuated seal for a tube. A wall made of an elastomer and having an opening is expanded by several levers during the insertion of an instrument into the tube, as a result of which the opening is enlarged.

U.S. Pat. No. 5,366,446 describes an introducer assembly for use on the skin of a patient, said assembly being designed for the insertion of tubes with different external diameters. The assembly comprises a membrane made of a pierceable elastomer material and arranged in the center of a bellows.

EP 0 630 660 A1 describes a seal assembly for accommodating a surgical instrument. The seal assembly comprises a duckbill seal or an arrangement composed of a plurality of sealing elements which are partially slit in a star shape and which partially overlap one another and are partially conical.

EP 0 746 359 B1 describes a catheter check valve. For sealing purposes, a rubber seal with an aperture is provided and, in the distal direction from this, a duckbill valve with a rectilinear slit.

WO 2010/045702 A1 describes a disposable seal for a tube, The disposable seal has an approximately cup-shaped design with intersecting slits at the base.

U.S. Pat. No. 4,430,081 describes a cannula for use with angiography catheters. To provide a seal against the entry of air or against the escape of blood from a blood vessel, a first seal with a slit, a second seal with a hole, and a third seal with a flapper in it are provided, which seals are arranged adjoining one another.

WO 91/12838 A1 proposes an infusion port with a plurality of elastic disks which are arranged one after another and which each have circular openings or have star-shaped slits offset in rotation relative to one another.

EP 0 536 549 A1 describes a trocar sleeve for the passage of a medical instrument. A sealing device for sealing an axial passage and a hollow shank, both when an instrument is inserted and also when an instrument is not inserted, comprises one or more partition walls made of elastic material with intersecting slits offset relative to each other.

WO 94/01149 A1 and DE 693 29 286 T2 describe a valve for an introducer assembly. A body made of silicone or of another elastomer material comprises a cylindrical wall, which encloses a bore. One end of the cylindrical wall and of the bore is closed by a wall with a centrally arranged opening. The other end of the cylindrical wall and of the bore is closed by two mutually inclined leaflets with a slit lying between them.

WO 98/32484 A1 describes catheter insertion equipment with a hemostatic valve. A sealing element comprises two holed support disks, between which is provided a sealing disk made of a soft, elastic foam plastic with radially extending slits.

EP 1 269 925 A1 describes an access cannula for endoscopic operations. A twin-disk valve comprises two disks, each of them with a star-shaped slit with three arms, wherein the slits of the two disks are offset in rotation relative to each other.

EP 1 350 476 A1 describes a trocar sleeve with a valve. The valve comprises an insertion region with angled wall sections running toward each other in the distal direction, and with sealing lips lying elastically against each other.

The described sealing devices each have specific advantages and disadvantages. For many fields of use, satisfactory solutions have not yet been found, or at least further improvements are desirable. This is particularly the case in view of the fact that a sealing device is intended to satisfy numerous requirements simultaneously. For example, the sealing device should be fluid-tight, robust, re-usable and in particular autoclavable, should offer the least possible resistance to a movement of a medical instrument in the axial direction, should permit lever manipulation or tilting of a medical instrument inserted into the sealing device and also remain fluid-tight, should not turn inside out either during the insertion or during the removal of a medical instrument, and should be able to be produced cost-effectively.

SUMMARY OF THE INVENTION it is an object of the present invention to make available an improved sealing device which in particular meets the listed requirements and expectations to equal degrees.

This object is achieved by the subjects of the independent claims.

Developments are set forth in the dependent claims.

A sealing device for sealing a passage for a medical instrument comprises a fastening area for fastening the sealing device on a tube or another medical appliance; a sealing area which is at least either designed to bear on the circumference of a medical instrument inserted into the sealing device or is designed to close the sealing device when no medical instrument is inserted into the sealing device; a first elastic wall enclosing the sealing area in a ring shape, with an annular first edge, which is connected to the sealing area, and an annular second edge; a second elastic wall which encloses the first wall in a ring shape and is spaced apart therefrom, with an annular first edge and an annular second edge, which is connected to the fastening area; an annular transition area, which connects the second edge of the first wall to the first edge of the second wall, wherein the transition area has a wall thickness greater than the first wall and greater than the second wall.

The sealing device is in particular a sealing device for a tube of a trocar which, during a microinvasive intervention, forms an access to a cavity. Alternatively, the sealing device is provided and designed for a work channel of an endoscope or for another medical appliance into which a medical instrument can be inserted and which is intended to be closed in a fluid-tight manner with and without the medical instrument. The sealing area is provided in particular at the proximal end or on the proximal face of the sealing device.

The fastening area is provided in particular at the distal end or on the distal face of the sealing device. The fastening area is provided and designed in particular for releasably fastening the sealing device on the proximal end of a tube or of a work channel of an endoscope or of another medical appliance. For this purpose, the fastening area comprises in particular an elastic collar or another surface portion that permits a form-fit mechanical connection to a correspondingly configured surface portion on the medical appliance. In particular, the sealing device comprises an annular, inwardly protruding collar, which is designed to engage in an annular, outwardly open groove on a medical appliance, or it comprises an annular, inwardly open groove, which is designed to receive an outwardly protruding collar on a medical appliance.

The first wall and the second wall are each substantially circular, elliptic or polygonal, for example. In particular, the first wall and the second wall each have substantially the shape of an annular cutout of an envelope of a cylinder or of a cone with a circular, elliptic or polygonal or other base surface or cross section.

The second wall is in particular spaced apart radially from the first wall. The first wall and the second wall are in particular parallel or substantially parallel (angle not greater than 10 degrees or not greater than 20 degrees) to each other. Both the first and also the second elastic wall can each have a constant wall thickness, or a wall thickness increasing or decreasing from the proximal end to the distal end.

The first edge and the second edge of each wall are in particular circular in each case. The first edge of the first wall is in particular connected directly to the ring seal and directly, or indirectly via the ring seal, to the edge of the slit membrane. The second edge of the first wall can be connected directly or indirectly to the fastening area. In particular, the annular transition area connects the second edge of the first wall and the first edge of the second wall in the radial direction.

The wall thickness is in particular the distance between two mutually opposite points on the two surfaces of the wall directed away from each other. In particular, and at least in simple cases, two points lie opposite each other when a straight line through both points is perpendicular to at least one of the two surfaces of the wall directed away from each other The increased wall thickness in the transition area of the sealing device results in increased stiffness of the transition area. This increased stiffness in the transition area reduces deformations of the sealing device in the transition area. An increased stiffness of the transition area reduces the risk of the sealing device turning inside out starting from the transition area. A medical instrument in the sealing device can therefore be moved in both directions, i.e. both in the distal direction and also in the proximal direction, with less risk of the sealing device turning inside out.

In a sealing device as described here, the greatest wall thickness of the transition area is in particular at least 50 percent greater than the minimum wall thickness of the second wall.

The greatest wall thickness of the transition area is therefore in particular 1.5 times the minimum wall thickness of the second wall. In particular, the greatest wall thickness of the transition area is 1.5 times to 2 times and or 1.6 times to 1.8 times the minimum wall thickness of the second wall. In particular, the minimum wall thickness of the second wall lies near the transition area or at the boundary between the second wall and the transition area.

In a sealing device as described here, the wall thickness of the first wall increases in particular from the sealing area to the transition area.

In particular, the wall thickness of the first wall increases continuously, or as a constant or even strictly monotonically increasing function of location, from the sealing area to the transition area.

In a sealing device as described here, the thickness of the second wall increases from the transition area to the fastening area.

In particular, the wall thickness of the second wall increases continuously, or as a constant or even strictly monotonically increasing function of location, from the transition area to the fastening area.

A continuous increase of the wall thickness and in particular a variation of the wall thickness as a strictly monotonic function of location may not only be advantageous from the point of view of manufacturing technology, it may also avoid mechanical stress concentrations during a deformation of the sealing device.

In a sealing device as described here, the transition area, particularly in a sectional plane containing an axis of symmetry of the first wall and of the second wall, has a substantially arc-shaped cross section.

The cross section is in particular substantially semicircular. A configuration of the transition area with an arc-shaped cross section avoids local mechanical stress concentrations in the event of a deformation of the sealing device and thus improves the mechanical robustness and the useful life of the sealing device.

In a sealing device as described here, the sealing area comprises in particular a slit membrane for closing the sealing device when no medical instrument is inserted into the sealing device, and a ring seal designed to bear on the circumference of a medical instrument inserted into the sealing device, wherein an outer edge of the slit membrane is arranged directly behind the ring seal with respect to the direction of insertion in which a medical instrument is to be inserted into the sealing device.

The ring seal is adapted, particularly in terms of its geometric properties, to a shank of a predefined medical instrument or a predefined shank cross section of a medical instrument. The ring seal can be designed to exhibit a shape similar to a torus in the relaxed state, or when no medical instrument is inserted into the sealing device. Alternatively, the ring seal can exhibit a shape similar to a torus when a medical instrument is inserted into the sealing device. In particular, when a medical instrument is inserted into the sealing device, the ring seal is designed to have a convex cross section at least in its area adjoining the medical instrument, in relation to a section along a plane that contains the longitudinal axis of the medical instrument.

The ring seal and the slit membrane are in particular designed to jointly form a substantially cup-shaped surface portion of the sealing device when no medical instrument is inserted into the sealing device.

In the proximal direction and the distal direction, the slit membrane has in particular two parallel or substantially parallel surfaces. The slit membrane is in particular plane or substantially plane. The slit membrane has in particular a slit with three or more radially extending portions at equal or substantially equal angular distances.

The features of the sealing device can permit a fluid-tight closure of a tube or of another medical appliance by the slit membrane when no medical instrument is inserted into the sealing device, or by the ring seal when a medical instrument is inserted into the sealing device. Since both the ring seal and also the slit membrane are arranged on the same first edge of the first wall and are connected to the fastening area by the first wall and the second wall, the elasticity of the first wall and of the second wall means that, even in the event of a movement of the medical instrument in a direction perpendicular to the direction of insertion, no substantially increased forces act between the medical instrument on the one hand and the ring seal and the slit membrane on the other hand. The sealing action of the slit membrane and especially of the ring seal bearing on the circumference of the medical instrument is therefore not influenced or not appreciably influenced by tilting or lever movements of the medical instrument. The fluid-tight nature of the sealing device can therefore be ensured even in a practical application in which the sealing action of other sealing devices is compromised or impaired by forces between the instrument and the sealing device.

The direction of insertion is in particular perpendicular to the first edge and perpendicular to the second edge of the first wall.

The elasticity of the first wall and of the second wall, and the resulting comparatively low forces between a medical instrument inserted into the sealing device on the one hand and the slit membrane and the ring seal on the other hand, can also reduce the risk of damage to the ring seal or to the slit membrane. The sealing device can therefore have a particularly high degree of reliability and a particularly long useful life. A re-usable configuration of the sealing device may therefore be expedient and contribute to low life-cycle costs.

Arranging the slit membrane in direct proximity to the ring seal can support the described effect of the elasticity of the first wall. In this case, only comparatively low forces act on the ring seal and on the slit membrane, not only when a medical instrument moves in a direction perpendicular to the direction of insertion, but also when the medical instrument tilts about an axis perpendicular to the direction of insertion. An arrangement of the slit membrane behind the ring seal with respect to the direction of insertion allows the ring seal bearing on the circumference of a medical instrument to have a sealing effect even before the medical instrument opens the slit membrane.

A one-piece configuration of ring seal and slit membrane (in particular on a single casting) can reduce the manufacturing costs, can allow a smaller overall size and can improve the mechanical robustness of the sealing device.

A sealing device as described here also comprises in particular a reinforcement at the end of a slit in the sealing membrane.

The reinforcement is designed, for example, in the form of a locally increased wall thickness or material thickness of the sealing membrane in the area of the end of a slit. Such a reinforcement can reduce the risk of the sealing membrane tearing at an end of the slit and can thus increase the robustness and useful life of the sealing device.

A sealing device as described here also comprises in particular a tab near the fastening area, for manually releasing the fastening of the sealing device on a tube or another medical appliance.

The tab allows the sealing device to be gripped easily, securely and ergonomically when manually connecting the sealing device to a tube or another medical appliance and especially when manually separating the sealing device from the tube or the other medical appliance. Arranging the tab at or near the fastening area of the sealing device can have the effect that a manually generated tensile force acts very directly on the fastening area. Thus, for example, an inwardly protruding collar on the sealing device can be easily and safely pulled out of an outwardly open groove on a medical appliance, in order to undo a mechanical connection of sealing device and medical appliance.

A sealing device as described here is in particular configured in one piece.

In particular, the sealing device is designed as a cast part from silicone or another elastic, biocompatible and autoclavable material. A one-piece design of the sealing device can aid simple dismantling and cleaning of the sealing device. Compared to a multi-piece design, a one-piece design of the sealing device can also permit lower costs for production, storage and logistics.

A sealing device as described here also comprises in particular a friction-reducing layer on a surface area that is designed to touch a medical instrument inserted into the sealing device.

In particular, a friction-reducing layer is provided on the entire surface of the sealing device or at least in the area of the ring seal and/or of the slit membrane. A friction-reducing layer can reduce the forces that act when inserting an instrument into the sealing device and when withdrawing the instrument from the sealing device. The layer can reduce both the static friction and also the kinetic friction. A reduction of the kinetic and/or static friction can allow a more sensitive movement of a medical instrument in the sealing device and can reduce mechanical loading of the sealing device. Reduced mechanical loading of the sealing device can reduce the risk of the first wall turning inside out and the risk of the sealing device suffering damage, for example tearing.

The friction-reducing layer comprises in particular poly (p-xylylene), which is also sold under the brand name Parylene.

The sealing device has in particular one or more webs, which are distributed uniformly about the circumference of the first wall and which at least in part are oriented in the direction from the first edge to the second edge of the first wall. The web, or each one of the webs, is at least connected either to the first wall or to the second wall. The webs reach in particular from the first edge to the second edge of the first wall. The web or the webs extend in particular across part of the space between the first wall and the second wall.

The first wall the second wall and the one or more webs are in particular elastically deformable, in such a way that a movement of the sealing area relative to the fastening area is possible in directions perpendicular to the direction in which a medical instrument can be inserted into the sealing device. Moreover, the first wall, the second wall and the one or more webs can be elastically deformable in such a way that they allow the ring seal and the slit membrane to pivot relative to the fastening area.

The one or more webs are at least in part arranged and oriented parallel to the direction of insertion. Alternatively or in addition, the one or more webs are at least in part configured helically with respect to the direction of insertion. Moreover, the one or more webs can be configured radially or at least in part tangentially with respect to the first wall and/or the second wall.

The first wall and the second wall form in particular a fold of (planar) bellows. It may be advantageous that the second wall has less elasticity than the first wall. For this purpose, the second wall has in particular a greater wall thickness than the first wall.

A tube comprises a sealing device as described here.

The tube is in particular the tube or the sleeve of a trocar which, after an opening or an access route has been created, remains in the latter. In particular, apart from the sealing device, the tube has no further sealing device for closing the tube when a medical instrument is inserted into the tube or for closing the tube without an inserted medical instrument.

BRIEF DESCRIPTION OF THE DRAWINGS

Embodiments are explained in more detail below with reference to the attached figures, in which:

FIG. 4 shows a schematic sectional view of the sealing device from FIG. 3;

FIG. 5 shows a further schematic sectional view of the sealing device from FIGS. 3 and 4;

FIG. 6 shows a further schematic view of the sealing device from FIGS. 3 to 5.

DETAILED DESCRIPTION OF THE INVENTION

Figure 1:
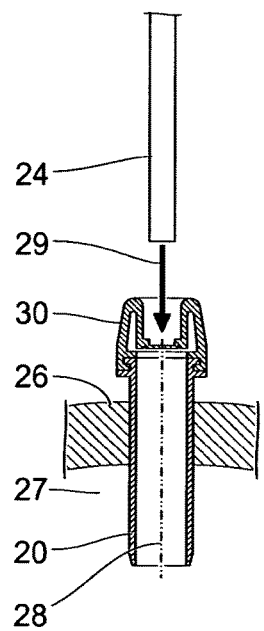
FIG. 1 shows a schematic view of a tube of a trocar with a sealing device and a medical instrument.
Figure 2:
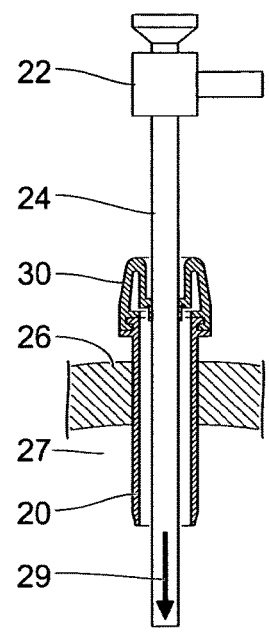
FIG. 2 shows a further schematic view of the tube with the sealing device and the medical instrument.

FIGS. 1 and 2 show schematic sectional views of a tube 20 of a trocar, which is fitted into an abdominal wall 26 of a patient. Through the lumen of the tube 20, one or more medical instruments can be inserted into a cavity 27 under the abdominal wall 26 of the patient. The tube 20, the abdominal wall 26 and the cavity 27 under the abdominal wall 26 are shown in a section along a plane containing a longitudinal axis 28 of the tube 20. In particular, the tube 20 is at least in part rotationally symmetrical with respect to the longitudinal axis 28. The tube 20 comprises a sealing device 30 at its proximal end outside the cavity 27. Embodiments of the sealing device 30 are described in detail with reference to FIGS. 3 to 8.

FIGS. 1 and 2 also show a medical instrument 22 with a shank 24. Since the internal design of the medical instrument 22 and of the shank 24 thereof are not relevant as regards the properties of the tube 20 that are described below, only contours of the medical instrument 22 and of the shank 24 thereof are depicted for simplicity. The medical instrument 22 is shown by way of an example as an endoscope in FIG. 2.

The shank 24 of the medical instrument 22 can be inserted into the tube 20 in a direction 29 parallel or substantially parallel to the longitudinal axis 28 of the tube 20. The shank 24 of the medical instrument 22 is shown in FIG. 1 before insertion into the tube 20 or into the lumen thereof and is shown in FIG. 2 after insertion into the tube 20 or into the lumen thereof. The sealing device 30 closes the proximal end of the tube 20 in a fluid-tight manner both when, as is shown in FIG. 1, no medical instrument is inserted into the tube 20 and also when, as is shown in FIG. 2, a medical instrument 22 is inserted into the tube 20. In this way, the sealing device 30 prevents escape of a gas or of another fluid from the cavity 27 under the abdominal wall 26 of the patient.

Figure 3:
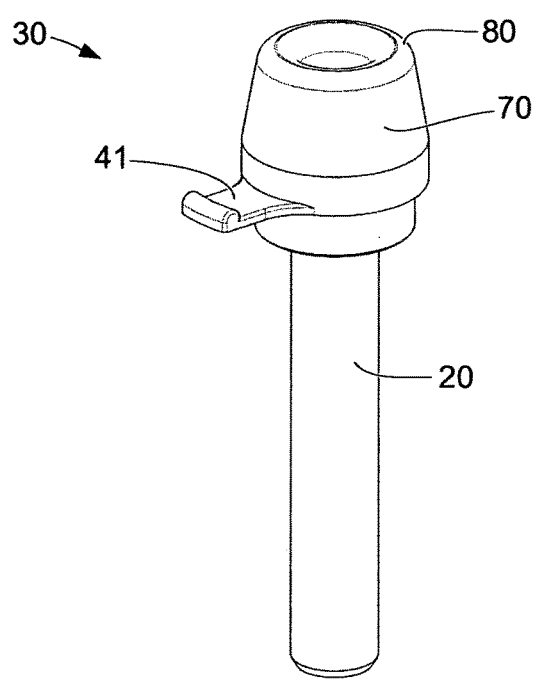
FIG. 3 shows a schematic axonometric view of a further tube with a further sealing device.

FIG. 3 shows a schematic axonometric view of a further illustrative embodiment of a tube 20 with a sealing device 30. The sealing device 30 of the illustrative embodiment in FIG. 3 differs from the sealing device shown in FIGS. 1 and 2 particularly in terms of a tab 41 near a proximal end of the sealing device 30. Apart from the tab, the sealing device described above with reference to FIGS. 1 and 2 can have similar or identical properties to the sealing device described below with reference to FIGS. 3 to 6.

FIG. 4 shows a schematic sectional view of the sealing device from FIG. 3. The sealing device 30 is shown in section along a plane containing the longitudinal axis 28 of the tube 20.

The sealing device 31 is configured in one piece, in particular cast from silicone or another elastic material. The sealing device 30 comprises a sealing membrane 31. The sealing membrane 31 is substantially circular and is arranged symmetrically with respect to the longitudinal axis 28. The sealing membrane 31 has two substantially plane and parallel faces or surfaces on the proximal side and distal side. Moreover, the sealing membrane 31 has a slit 32 composed of three portions which are arranged substantially symmetrically with respect to one another and radially, of which one lies in the sectional plane of FIG. 3 (to the right of the longitudinal axis 28).

The circular edge 33 of the sealing membrane 31 merges into an area of the sealing device 30 designed as a ring seal 34. The area of the sealing device 30 forming the ring seal 34 is substantially circular and has a cross section that ensures a suitable elasticity of the ring seal 34. In the relaxed state of the sealing device 30 shown in FIG. 3, the sealing membrane 31 and the ring seal 34 form a sealing area in the shape of a shallow cup, of which the base forms the sealing membrane 31 and of which the wall and edge form the ring seal 34.

The ring seal 34 merges radially outward into a first elastic wall 60, which has substantially the shape of an annular cutout of an envelope of a circular cylinder or an envelope of a cone. A first edge 61 of the first wall 60 is connected to the ring seal 34.

The sealing membrane 31, the ring seal 34 and the first elastic wall 60 of the sealing device 30 are surrounded substantially in a ring shape by a second elastic wall 70. The second wall 70 has substantially the shape of an annular cutout of an envelope of a circular cylinder or an envelope of a cone. A transition area 80 connects the second edge 62 of the first wall 60 to a first edge 71 of the second wall 70, A second edge 72 of the second wall 70 merges into an edge profile 39 in the form of a collar that protrudes radially inward toward the longitudinal axis 28.

The direction from the first edge 61 of the first wall 60 or from the sealing area 31, 34 to the second edge 62 of the first wall or to the transition area 80 is counter to the direction from the first edge 71 of the second wall or from the transition area 80 to the second edge 72 of the second wall 70 or to the edge profile 39. The sealing area 31, 34 therefore lies closer to the edge profile 39 than the transition area 80. The first wall 60, the transition area 80 and the second wall 70 form a structure with a U-shaped cross section.

In the example shown, the wall thickness of the first wall 60 increases from the first edge 61 or from the sealing area 31, 34 to the second edge 62 or to the transition area 80. In the example shown, the wall thickness of the second wall 70 increases from the first edge 71 or from the transition area 80 to the second edge 72. In the example shown, both the wall thickness of the first wall 60 and also the wall thickness of the second wall 70 is in each case a monotonic, in particular affine-linear function of the location or of a coordinate measured parallel to the longitudinal axis 28.

The elasticity of the walls 60, 70 permits a movement of the sealing area composed of sealing membrane 31 and ring seal 34 on the one hand with respect to the fastening area formed by the edge profile 39 and on the other hand particularly in directions perpendicular to the longitudinal axis 28, The elasticity of the walls 60, 70 can be adjusted within wide ranges through the choice of the material of the sealing device 31 and of the wall thicknesses of the walk 60, 70.

In the sectional plane shown in FIG. 4 and containing the longitudinal axis 28, the transition area 80 between the first wall 60 and the second wall 70 has substantially the shape of a semicircular arc. The width of this semicircular arc or the wall thickness of the transition area varies. Starting from the second edge 62 of the first wall 60, the wall thickness of the sealing device 30 in the transition area 80 initially increases to a maximum wall thickness and then decreases again toward the first edge 71 of the second wall 70.

The maximum wall thickness lies at or near the apex 81 of the transition area 80 and in particular measures between ca. 115 percent and ca 135 percent (ca. 5/4) of the wall thickness of the first wall 60 near the second edge 62 thereof and between ca. 140 percent and ca. 180 percent (ca. 5/3) of the wall thickness of the second wall 70 near the first edge 71 thereof, In the example shown, the wall thickness varies both inside the transition area 80 and also between the transition area 80 and the second edge 62 of the first wall 60 and between the transition area 80 and the first edge 71 of the second wall 70, in each case continuously.

In a departure from the illustration in FIG. 4, the wall thickness of the sealing device 30 both in the area of the first wall 60 and also in the area of the second wall 70, and also in the transition area 80, can in each case vary discontinuously or in steps. Moreover, the wall thickness between the first wall 60 and the transition area and/or between the second wall 70 and the transition area 80 can vary or change in steps.

Moreover, in a departure from the illustration in FIG. 4, the transition area 80 can have a configuration that is not arc-shaped. For example, the transition area can have a rectangular or substantially rectangular or a circular or substantially circular cross section. In each case, an increased wall thickness in the transition area 80 results in increased mechanical stiffness of the transition area 80 and thereby reduces the probability of the sealing device turning inside out starting from the transition area 80.

In a departure from the illustration in FIG. 4, it is possible, in the space between the first wall 60 and the second wall 70, for webs to be arranged on the first wall 60. In particular, these webs are substantially plate-shaped, are oriented radially and parallel to the longitudinal axis 28 or are in a helical configuration. Moreover, the webs can be arranged and oriented tangentially to the first wall 60 and/or can be connected to the second wall 70.

FIG. 5 shows a schematic view of a section through the sealing device 30 shown in FIGS. 3 and 4, along the plane A-A indicated in FIG. 4 and perpendicular to the longitudinal axis 28.

FIG. 5 shows the sealing device 30 without an inserted medical instrument and therefore in a state similar to the illustration in FIG. 3. The sealing membrane 31 with the star-shaped slit 32 appears in plan view. At the three ends of the three symmetrically arranged radial portions of the slit 32 in the sealing membrane 31, reinforcements 36 (not shown in FIGS. 1 to 4) are provided in the form of small areas of thickening 36 of the sealing membrane 31. The reinforcements 36 prevent or reduce the risk of the sealing membrane 31 tearing at the ends of the slit 32 as a result of the notch effect.

Apart from the reinforcements 36, the proximal surface of the sealing membrane 31 facing toward the observer and the distal surface thereof facing away from the observer are substantially plane-parallel. The sealing membrane 31 closes the sealing device in a fluid-tight or substantially fluid-tight manner since, in the relaxed state shown, it forms a substantially plane plate perpendicular to the longitudinal axis and parallel to the plane of the drawing of FIG. 5.

FIG. 6 shows another schematic view of the sealing device 30 shown in FIGS. 3 to 5. FIG. 6 is a plan view, the plane of the drawing being parallel to the sectional plane A-A of FIG. 5. The viewing direction of FIG. 6 is the opposite of the viewing direction of FIG. 5, that is to say FIG. 6 shows the distal face of the sealing device 30.

FIG. 6 shows the sealing device 30 with a shank 24 of a medical instrument inserted into the sealing device 30. Similarly to the view in FIG. 4, the membrane 31 is elastically deformed and bears on the circumference of the shank 24 in three portions defined by the star-shaped slit 32 (see FIG. 6). The three parts of the sealing membrane 31 formed by the star-shaped slit 32 are here deformed from the plane shape discernible in FIG. 4 to the shape of cutouts of an envelope of a circular cylinder and bear on the outer circumference of the shank 24.

By virtue of the elastic deformation of the slit sealing membrane 31 and of the transition area between the edge of the slit sealing membrane 31 and the ring seal 34, the ring seal 34 bears on the medical instrument, like a conventional O-ring seal, substantially linearly along a circular line enclosing the shank 24 of the medical instrument and thus forms a fluid-tight seal.

In FIGS. 1, 2 and 3, a tube is shown with only one sealing device 30. Alternatively, a plurality of sealing devices 30 can be provided alongside one another on a tube 20, such that a plurality of medical instruments 22 can be inserted simultaneously and alongside one another into the tube in a fluid-tight manner. This can permit microinvasive procedures through a single access. For this purpose, the sealing devices 30 are connected to the proximal end of the rigid tube of the tube in particular via an elastic connection piece.

LIST OF REFERENCE SIGNS 20 tube of a trocar
22 medical instrument
24 shank of the medical instrument
26 abdominal wall of a patient
27 cavity under the abdominal wall 26
28 longitudinal axis of the tube 20
29 direction of insertion of a medical instrument 22 into the tube 20
30 sealing device 31 sealing membrane of the sealing device 30
32 slit in the sealing membrane 31
33 edge of the sealing membrane 31
34 ring seal
36 reinforcement at an end of the slit 32 in the sealing membrane 31
39 edge profile on the sealing device 30
41 tab
60 first elastic wall
61 first edge of the first wall 60
62 second edge of the first wall 60
70 second elastic wall
71 first edge of the second wall 60
72 second edge of the second wall 60
80 transition area between second edge 62 of the first wall 60 and first edge 71 of second wall 70
81 apex of the transition area

The invention claimed is:

1. A sealing device for sealing a passage for a medical instrument, with:
   a fastening area for fastening the sealing device on a tube or another medical appliance;
   a sealing area which is at least either designed to bear on the circumference of a medical instrument inserted into the sealing device or is designed to close the sealing device when no medical instrument is inserted into the sealing device;
   a first elastic wall enclosing the sealing area in a ring shape, with an annular first edge, which is connected to the sealing area, and an annular second edge;
   a second elastic wall which encloses the first wall in a ring shape and is spaced apart therefrom, with an annular first edge and an annular second edge, which is connected to the fastening area;
   an annular transition area, which connects the second edge of the first wall to the first edge of the second wall, wherein the transition area has a wall thickness greater than the first wall and greater than the second wall;
   wherein the sealing area comprises a slit membrane for closing the sealing device when no medical instrument is inserted into the sealing device, and a ring seal designed to bear on the circumference of a medical instrument inserted into the sealing device; and
   an outer edge of the slit membrane is arranged directly behind the ring seal with respect to the direction of insertion in which a medical instrument is to be inserted into the sealing device.

2. The sealing device according to claim 1, in which the greatest wall thickness of the transition area is at least 50 percent greater than the minimum wall thickness of the second wall.

3. The sealing device according to claim 1, in which the thickness of the first wall increases from the sealing area to the transition area.

4. The sealing device according to claim 1, in which the thickness of the second wall increases from the transition area to the fastening area.

5. The sealing device according to claim 1, in which the transition area, in a sectional plane containing an axis of symmetry of the first wall and of the second wall, has a substantially arc-shaped cross section.

6. The sealing device according to claim 1, also with:
   a reinforcement at an end of a slit in the slit membrane.

7. The sealing device according to claim 1, also with:
   a tab near the fastening area, for manually releasing the fastening of the sealing device on the tube or another medical appliance.

8. The sealing device according to claim 1, wherein the sealing device is configured in one piece.

9. The sealing device according to claim 1, also with:
   a friction-reducing layer on a surface area that is designed to touch a medical instrument inserted into the sealing device.

10. A tube with a sealing device according to claim 1.

11. The tube according to claim 10, wherein the tube has, other than the sealing device, no further sealing device for closing the tube when a medical instrument is inserted into the tube or for closing the tube without an inserted medical instrument.

12. The sealing device according to claim 1, wherein the slit membrane comprises three symmetrically arranged radial portions.

13. The sealing device according to claim 12, further comprising a reinforcement at an end of each slit separating the radial portions.

14. The sealing device according to claim 1, wherein the ring seal comprises an O-ring.

\* \* \* \* \*